United States Patent [19]

Rogers et al.

[11] Patent Number: 5,066,125
[45] Date of Patent: Nov. 19, 1991

[54] ELECTROTHERMAL DIRECT INJECTION TORCH FOR INDUCTIVELY COUPLED PLASMA

[75] Inventors: Michael D. G. Rogers; William B. Henderson, both of Torrance, Calif.

[73] Assignee: Geochemical Services, Inc., Rocklin, Calif.

[21] Appl. No.: 436,970

[22] Filed: Nov. 15, 1989

Related U.S. Application Data

[63] Continuation of Ser. No. 191,723, May 6, 1988, abandoned, which is a continuation of Ser. No. 23,069, Mar. 6, 1987, abandoned.

[51] Int. Cl.⁵ ...................... G01N 21/73; G01N 21/74
[52] U.S. Cl. ...................................... 356/316; 356/312
[58] Field of Search ................................ 356/312, 316

[56] References Cited

U.S. PATENT DOCUMENTS

| | | | |
|---|---|---|---|
| 3,484,650 | 12/1969 | Rendina | 356/316 X |
| 3,843,257 | 10/1974 | Wooten | 356/316 |
| 4,225,235 | 9/1980 | Anderson et al. | 356/316 |
| 4,509,855 | 4/1985 | Gay | 356/316 X |
| 4,556,318 | 12/1985 | Barnes et al. | 356/316 |
| 4,567,389 | 4/1987 | Littlejohn | 356/312 |
| 4,575,609 | 3/1986 | Fassel et al. | 356/316 X |
| 4,833,322 | 5/1989 | Forster et al. | 356/316 |

FOREIGN PATENT DOCUMENTS 2023336 12/1971 Fed. Rep. of Germany ...... 356/312

OTHER PUBLICATIONS

Applied Spectroscopy, vol. 40, No. 3, 1986, Society for Applies Spectroscopy, Baltimore, Md., U.S., Y. Shao et al.: "Performance of a Direct Sample Insertion System for the Inductively Coupled Plasma", pp. 386-393.

Primary Examiner—Vincent P. McGraw
Attorney, Agent, or Firm—Spensley Horn Jubas & Lubitz

[57] ABSTRACT

An inductively coupled plasma spectroscopy apparatus is provided in which an inductively coupled plasma torch and an analyte sample atomizer are integrally formed as a single unit. The atomizer portion of the apparatus includes two electrodes and a plasma nozzle through which a heating element is placed. Test samples may be placed into a sample vessel which is positioned within the heating element. The torch portion includes a glass containment wall surrounding at least a portion of the plasma nozzle to define a plasma chamber located immediately adjacent to the sample vessel. The glass containment wall contains a radio frequency (RF) coil wrapped about its periphery which is inductively coupled to a supply of gas. A variable rate cooling manifold is also provided about the periphery of the containment wall. The integral design effectively reduces the buildup of memory condensate within the apparatus, thereby decreasing contamination and improving the sensitivity of the results obtained.

15 Claims, 1 Drawing Sheet

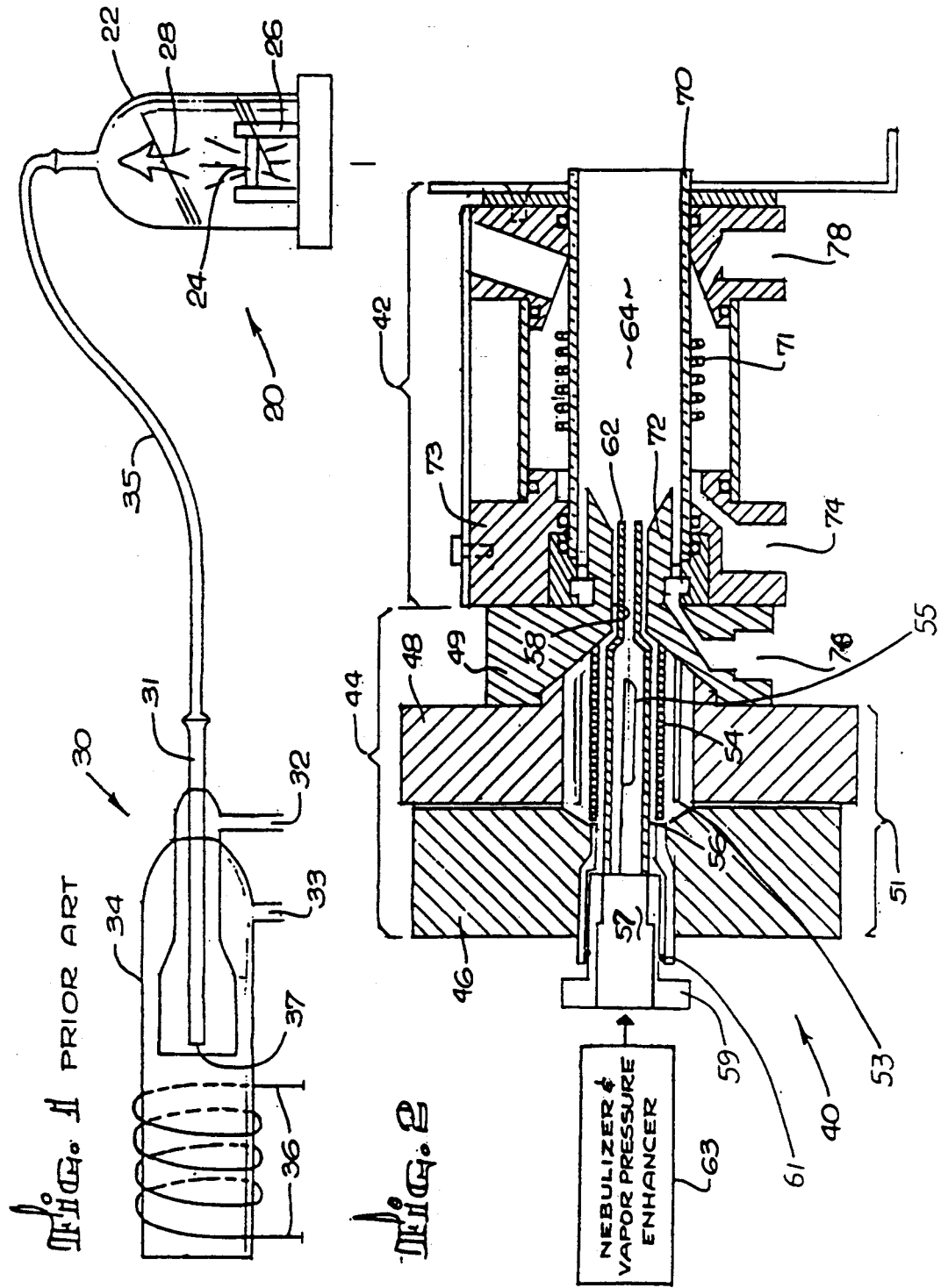

ELECTROTHERMAL DIRECT INJECTION TORCH FOR INDUCTIVELY COUPLED PLASMA

This is a continuation of application Ser. No. 07/191,723 filed on May 6, 1988, now abandoned, which was a continuation of application Ser. No. 07/023,069, filed Mar. 6, 1987, now abandoned.

BACKGROUND OF THE INVENTION

1. Field of the Invention

This invention relates generally to a plasma generating apparatus for use in plasma spectroscopy, and more specifically to an improved apparatus having an inductively coupled plasma torch and electrothermal atomizer.

2. Background Information

In inductively coupled plasma (ICP) spectroscopy, a procedure is utilized in which a sample of analyte (a material to be analyzed) is vaporized or atomized and passed into a plasma chamber where its spectra may be observed and analyzed.

As shown in FIG. 1, prior art ICP spectroscopy systems have typically included an electrothermal atomizer 20 interconnected with a separate ICP torch 30 by means of a long pipe, conduit or similar device 35. Typically, the atomizer 20 is composed of a large bell-shaped glass jar 22 which encases a carbon rod heater element 24 extending between two electrodes 26. The glass jar 22 may be lifted, whereupon a sample of analyte may be placed in the heater element 24 and the jar 22 replaced. The analyte is then heated to induce atomization of the analyte. As atomization commences, a supply of carrier gas 28 (such as argon) is flowed over the electrodes where it mixes with the atomizing analyte. The mixture flow within the bell jar 22 passes through the pipe or conduit 35 to the ICP torch 30.

A conventional ICP torch 30 is typically formed of quartz glass and includes intricate ducting. A main duct 31 is provided into which the analyte mixture flow may pass. An auxiliary duct 32 is also provided through which an auxiliary flow of argon or a similar gas may be introduced within a quartz glass containment wall 34. In addition, a coolant duct 33 is provided into which a coolant gas may be introduced. A conventional ICP torch also has a radio frequency (RF) induction coil 36 which is wrapped about the containment wall 34. When energized, the induction coil 36 generates plasma out of the gas introduced through the auxiliary duct 32. Upon injection of the analyte mixture from the atomizer 20 into the of main duct, the mixture passes through the injector tip 37 of the torch 30 where it mixes with the plasma. The analyte mixture is thus heated up to the temperature of the plasma, wherein most of the molecules are ionized so that the mixture may be analyzed.

Another common prior art spectroscopy system provides for the interconnection of a spray chamber rather than an atomizer to an ICP torch by means of a pipe or conduit similar to the one described above. A liquid analyte then may be placed within the spray chamber where it may be converted into a fine spray for introduction to the ICP torch 30.

Prior art conventional ICP spectroscopy systems such as those described above typically suffer from several disadvantages. First and foremost, a myriad of locations exist within the system at which analyte may accumulate as condensation after completion of an analysis. This causes the system to have a "memory" that may cause contamination of subsequent analytes. These locations include, but are not limited to, (1) the walls of the atomizer 20; (2) the pipe or conduit 35 interconnecting the atomizer 20 or a spray chamber and the ICP torch 30; (3) the injector tip 37 of the ICP torch 30; and (4) the quartz glass containment wall 34 of the ICP torch 30.

A further disadvantage of the above-described systems is the severe signal loss which occurs between the atomizer 20 or spray chamber and the ICP torch 30 as a result of condensation. Since the path between the atomizer 20 or spray chamber and the containment wall 34 of the ICP torch 30 is long and condensate accumulates along the entirety of this path, only a relatively small portion of the analyte ever reaches the plasma chamber to be analyzed, creating a greater than desirable signal loss in results.

A further disadvantage of the above-described prior art ICP spectroscopy systems is their inadaptability to robotic sample loading. Vaporization of the analyte typically occurs under sealed glassware. Robotic systems, however, are not typically suited to operate in environments where glassware is encountered.

SUMMARY OF THE INVENTION

The present invention relates to an ICP spectroscopy apparatus in which an electrothermal atomizer and an ICP torch are integrated as a single unit. The apparatus is constructed using two adjacent annular electrodes through which an annular heater and a sample vessel may be removably inserted. A sample of analyte may be placed in the sample vessel and heated by the electrodes to atomize the analyte. The atomized analyte passes through a plasma nozzle into a plasma chamber portion of the ICP torch. A nebulizer gas jet and a vapor pressure enhancer are passed through the ICP spectroscopy apparatus to increase atomization of the analyte and to ensure maximum transfer of the atomized material into the plasma chamber of the ICP torch. A quartz glass plasma containment wall is provided about the plasma nozzle and is surrounded by a variable rate cooling manifold. A conventional radio frequency (RF) coil is wrapped about the containment wall and is inductively coupled to the gas within the plasma chamber.

An advantage of the present invention is the provision of an ICP torch/atomizer apparatus in which the amount of memory produced during analysis of a sample of analyte is mimimized, as are the number of locations at which memory condensate may accumulate.

A further advantage of the present invention is the provision of an ICP torch/atomizer apparatus in which the total volume of analyte passing to the ICP torch is increased, thereby increasing the sensitivity of the apparatus to a sample of analyte.

It is yet a further advantage of the present invention that an ICP torch/atomizer apparatus is provided in which an increased number of types of sample materials may be analyzed.

It is yet a further advantage of the present invention that an ICP torch/atomizer apparatus is provided which is adaptable to robotic sample loading.

It is yet a further advantage of the present invention that an ICP torch/atomizer apparatus is provided to which a conventional spray chamber may be connected.

The present invention will more readily be understood by reference to the description of the prefered embodiment set forth below in conjunction with the accompanying drawings.

BRIEF DESCRIPTION OF THE DRAWINGS

FIG. 1 is a side plan view of a prior art atomizer/ICP torch configuration.

FIG. 2 is a side cross-sectional plan view of the atomizer/ICP torch apparatus of the present invention.

DETAILED DESCRIPTION OF THE INVENTION

The invention will be described below with respect to the prefered physical embodiment. It will be apparent to those skilled in the art, however, that various improvements may be made without departing from the scope and spirit of the invention. Accordingly, the invention is not to be limited by the specific illustrative embodiment, but only by the appended claims.

FIG. 2 illustrates the preferred embodiment of the present invention. An integral ICP torch/electrothermal atomizer apparatus 40 is provided having a torch portion 42 and an electrothermal atomizer portion 44. The electrothermal atomizer portion 44 is composed of a first annular electrode 46, a second annular electrode 48, and a plasma nozzle 49. The first and second annular electrodes are interconnected to one another to form an electrode block 51 which may be removably attached to the plasma nozzle 49. The electrode contains an aperture 53 formed therethrough in which are housed an annular heating element 54 and an annular analytic sample vessel tube 56. The analytic sample vessel tube 56 extends through an aperture 58 in the plasma nozzle 49 and terminates to form an analyte injector tip 62 located immediately adjacent to a plasma chamber 64. A breech block 59 having a sample holder or spoon 55 at one end is removably insertable within the aperture 53. The breech block 59 may be maintained in sealing engagement with the electrode block 51 by means of an O-ring 61. A nebulizer jet represented schematically by numeral 63 having a vapor pressure enhancer (such as, for example, florine, chlorine, bromine, iodine, oxygen or sulphur) may be removably connected to the electrode block 51 at an aperture 57 formed through the breech block 59.

The torch portion 42 of the apparatus 40 contains a cylindrical quartz glass plasma containment wall 70, the interior of which defines the boundary of the plasma chamber 64. The plasma containment wall 70 surrounds a portion 72 of the plazma nozzle 49 such that the analyte injector tip 62 is located immediately adjacent to or within the plasma chamber 64. A cooling manifold 76 is provided through which a coolant gas (such as argon) may be continuously passed in order to prevent melting of the containment wall 70. A radio frequency (RF) coil 71 is provided which surrounds the containment wall 70 in order to allow inductive coupling to the gas passing through the plasma chamber 64. A variable rate cooling manifold 73 having an inlet duct 74 and an outlet duct 78 also surrounds the plasma containment wall 70. By passing a fluid of a preselected temperature through the inlet duct 74, selective heating or cooling of the the exterior of the plasma containment wall 70 may be obtained.

Operation of the above described integral ICP apparatus 40 occurs in the following manner. The integral breech block 59 and sample holder 55 are withdrawn from the atomizer portion 44 by robotic or other means (not shown). An analyte sample is placed within the sample holder 55 and the breech block 59 is replaced within the atomizer portion 44 with the sample holder 55 extending within the sample vessel tube 56. The electrode block 51 is then activated, raising the temperature of the sample vessel tube 56 and sample holder 55 to a point where atomization of the analyte commences.

The nebulizer jet 63 (argon in the present example) containing a vapor pressure enhancer is introduced through the aperture 57 of the electrode block 51. The argon gas and the vapor pressure enhancer pass over the heated analyte to ensure that maximum transfer of the atomized analyte occurs from the sample holder 55 through the sample vessel tube 56 into the plasma chamber 64. The RF coil 71 creates a plasma out of the argon coolant gas/vapor pressure enhancer/analyte mixture traveling into the plasma chamber 64. Since the plasma chamber 64 is located immediately adjacent to the analyte injector tip 62 of the sample vessel tube 56, no lengthy surface exists along which analyte may condense.

After analysis of the subject analyte, the exterior of the containment wall 70 is heated and condensate is removed by passing a fluid of high temperature through the variable rate cooling manifold 73. The coolant gas flowrate passing through the cooling manifold 76 may also be increased in order to quickly cool the interior of the containment glass wall 70.

As is apparent from the above description, the present invention is superior to prior art ICP torch/electrothermal atomizer configurations for a variety of reasons. First, buildup of analyte memory is prevented at virtually all of the locations at which condensate accumulated in prior art systems. The bell-shaped atomizer glass 22 is eliminated, and the length of the path between the atomizer and the torch is reduced to a minimum by placing the analyte injector tip 62 of the sample vessel 56 immediately adjacent to the plasma chamber 64. Moreover, the selected heating and cooling of the containment wall through the use of coolant gas within the boundaries of the containment wall and the heating of the variable rate cooling manifold at the outer surface of the containment wall effectively reduces condensate accumulation at this location.

Second, positioning of the analyte sample at a location immediately adjacent to the plasma chamber dramatically increases the sensitivity of the spectroscopy results which are obtained. This is accomplished by reducing the number of locations along the analyte path at which memory may accumulate, thus dramatically increasing the percentage of the atomized analyte which is ultimately tested.

Tests performed with a prototype of this apparatus have in fact produced greater than six orders of magnitude decay in signal between samples when compared to conventional ICP torch/atomizer systems in which decay of approximately three orders of magnitude between samples is common. As a result, a much wider range of sample concentrations may be analyzed sequentially without fear that analyte memory from prior analyses will influence the results of subsequent analyses. Less maintenance is therefore required for the system since cleaning of the various elements is not necessary as frequently. Moreover, additional operating time and better precision in results are obtained.

Third, the nebulizer jet 63 and the vapor pressure enhancer dramatically increase the rate at which the atomization of solid analyte occurs. It is therefore possible to atomize and subsequently observe the spectra of analyte which is in solid form, as well as conventional liquids and gases.

Fourth, elimination of the need for the use of a glass bell-jar atomizer 20 permits accommodation of efficient robotic sample loading. Since glass need not be handled in the present apparatus during the loading procedure, utilization of robotics is facilitated. Moreover, provision of the withdrawable sample holder 55 also improves the adaptability of the apparatus to autosampling since loading of analyte is a much less complex procedure than in conventional atomizers.

As another feature of the present invention, a conventional spray chamber capable of creating a fine spray of liquid analyte may be used without activation of the electrothermal atomizer portion 44. The conventional spray chamber may be connected to the aperture 57 of the electrode block 51. In this manner, liquid analyte may be vaporized by the spray chamber and may be passed directly to the torch portion 42 where its spectra may be observed. The ICP torch/atomizer apparatus 40 may thus be adaptable to be used as an ICP torch alone in conjunction with conventional analyte spray chambers.

Various modifications of the illustrated embodiment as well as other embodiments of the invention will be apparent to persons skilled in the art upon reference to this description. For example, means other than an inductively coupled plasma torch may be used to produce an analyte-bearing plasma, such as a microwave induced or capacitively coupled torch or the like. Moreover, the plasma may be contained within a predetermined boundary by other than a quartz glass containment wall, such as by magnetic means.

We claim:

1. A spectroscopy apparatus for atomizing and analyzing the spectra of test samples, comprising:
   electro-thermal atomization means for atomizing test samples, the atomization means having an outlet through which the atomized test samples may exit, and heating means for heating both the test sample and the outlet; and
   an inductively coupled plasma torch for ionizing and exciting the atomized test samples, said torch having a containment wall within which the atomized test samples are ionized and excited, the outlet of the atomizer means being located adjacent to or within the boundaries of the containment wall.

2. A spectroscopy apparatus for atomizing and analyzing the spectra of test samples, comprising:
   electro-thermal atomization means for atomizing test samples, the atomization means having an outlet through which the atomized test samples may exit; and
   an inductively coupled plasma torch for ionizing and exciting the atomized test samples, said torch having a containment wall within which the atomized test samples are ionized and excited, the outlet of the atomizer means being located within the boundaries of the containment wall;
   wherein the inductively coupled plasma torch includes variable cooling means for allowing the containment wall to be cooled at a variable rate.

3. A spectroscopy apparatus, comprising:
   an atomizer for atomizing a sample of analyte, the atomizer having an atomized sample conduit which defines an outlet, an analyte holder into which a sample of analyte may be placed, a heater for heating both the analyte holder and the sample conduit to atomize the sample in the holder, and an electrode portion for activating the heater; and
   a torch located adjacent to the atomizer for receiving the atomized sample from the atomizer sample conduit and for ionizing and exciting the atomized sample, the torch having a plasma chamber in which the atomized sample may be ionized and excited, wherein the outlet of the atomizer conduit extends into the plasma chamber of the torch.

4. A spectroscopy apparatus, comprising:
   an atomizer for atomizing a sample of analyte, the atomizer having an atomized sample conduit which defines an outlet, an analyte holder into which a sample of analyte may be placed, a heater for heating the both the analyte holder and the sample conduit to atomize the sample in the holder, and an electrode portion for activating the heater; and
   a torch located adjacent to the atomizer for receiving the atomized sample from the atomizer sample conduit and for ionizing and exiting the atomized sample, the torch having a plasma chamber in which the atomized sample may be ionized and excited, wherein the outlet of the atomizer conduit extends to a point adjacent to the plasma chamber of the torch.

5. A spectroscopy apparatus according to claim 4, wherein the torch further includes a containment means for containing the atomized sample within the plasma chamber.

6. A spectroscopy apparatus according to claim 5, wherein the containment means comprises a quartz glass containment wall.

7. A spectroscopy apparatus according to claim 5, wherein the containment means magnetically contains the atomized sample within the boundary of the plasma chamber.

8. A spectroscopy apparatus according to claim 5, wherein the containment means includes a containment wall and the torch further includes variable rate cooling means located adjacent to the containment wall for selectively heating and cooling the containment wall.

9. A spectroscopy apparatus according to claim 5, wherein the atomizer further includes a duct through which a cooling gas may be introduced into the plasma chamber of the torch for cooling the plasma chamber.

10. A spectroscopy apparatus according to claim 3, wherein the torch is an inductively coupled plasma torch.

11. A spectroscopy apparatus according to claim 3, wherein the torch is a capacitively coupled plasma torch.

12. A spectroscopy apparatus according to claim 3, further comprising a spray chamber directly interconnectable with the torch for allowing delivery of analyte from the spray chamber to the torch.

13. A spectroscopy apparatus according to claim 3, further comprising a nebulizer interconnectable with the atomizer, wherein the nebulizer passes a vapor pressure enhancing agent over the sample of analyte to increase the rate at which atomization of the sample of analyte occurs.

14. A spectroscopy apparatus according to claim 3, wherein the analyte holder is removable from the atomizer to facilitate loading of samples of analyte into the atomizer.

15. A spectroscopy apparatus, comprising:
   electrothermal atomizer means for atomizing an analyte, said electrothermal atomizer means having an atomized sample conduit which defines an outlet, said conduit being supported at one end so that the conduit outlet is cantilevered and free of heat sinks, said atomizer means further having an analyte holder within the sample conduit into which a sample of analyte may be placed, a heater exterior to the conduit for heating the conduit and the analyte holder within the conduit, and an electrode portion for activating the heater; and a torch located adjacent to the electrothermal atomizer means for ionizing and exciting the analyte, the torch having a plasma containment wall defining the boundary of a plasma chamber, wherein the outlet of the electrothermal atomizer extends to a point adjacent to or within the plasma chamber of the torch.

* * * * *